(12) United States Patent
Cushing (10) Patent No.: US 10,537,413 B2
(45) Date of Patent: Jan. 21, 2020

(54) METHOD AND FLASK FOR COLD POUR PROCESSING OF DENTAL PROSTHESIS

(71) Applicant: Charles John Cushing, Rock Hill, SC (US)

(72) Inventor: Charles John Cushing, Rock Hill, SC (US)

(73) Assignee: Charles John Cushing, Ringgold, GA (US)

( * ) Notice: Subject to any disclaimer, the term of this patent is extended or adjusted under 35 U.S.C. 154(b) by 341 days.

(21) Appl. No.: 15/721,863

(22) Filed: Sep. 30, 2017

(65) Prior Publication Data

US 2019/0099247 A1 Apr. 4, 2019

(51) Int. Cl.
*A61C 13/16* (2006.01)

(52) U.S. Cl.
CPC .................................... *A61C 13/16* (2013.01)

(58) Field of Classification Search
CPC .. A61C 13/16; A61C 9/00; B28B 7/02; B29C 33/301; B29C 33/302; B29C 33/306; B29C 33/307; B29C 33/308
USPC ........... 249/117–174, 203, 54; 425/175–180; 164/376; D24/176, 181
See application file for complete search history.

(56) References Cited

U.S. PATENT DOCUMENTS

| 2,188,415 A | * | 1/1940 | Malsch | A61C 13/16 425/180 |
| 2,440,910 A | * | 5/1948 | Opotow | A61C 13/16 425/180 |
| 2,471,205 A | * | 5/1949 | Fagan | A61C 13/16 425/180 |
| 2,574,593 A | * | 11/1951 | Scharfe | A61C 13/16 425/180 |
| 3,176,350 A | * | 4/1965 | Ryen | A61C 13/16 425/179 |
| 4,494,934 A | * | 1/1985 | Huffman | A61C 9/002 249/54 |
| 6,382,969 B1 | * | 5/2002 | Elnajjar | A61C 11/02 433/60 |
| 2002/0102514 A1 | * | 8/2002 | Huffman | A61C 9/002 433/34 |

FOREIGN PATENT DOCUMENTS

EP 2826440 A1 * 1/2015

* cited by examiner

*Primary Examiner* — Leith S Shafi (57) ABSTRACT

The present invention relates to an improved method of and dental flask, suitable for use with a dental reline jig for the purpose of cold pour acrylic processing of dentures, acrylic implant retained bridges and other dental prosthesis as well as any other manufactured products using conventional flask techniques and materials.

6 Claims, 11 Drawing Sheets

METHOD AND FLASK FOR COLD POUR PROCESSING OF DENTAL PROSTHESIS

FIELD OF THE INVENTION

The present method and invention in general relates to a flask made of aluminum or similar material for cold pour acrylics used to process dentures, acrylic dental prosthesis and acrylic implant retained bridges as well as any other manufactured products using conventional stone flask chambers in the lost wax technique.

BACKGROUND OF THE INVENTION

Cold pour acrylic, also called cold cure acrylic is used to make temporary dentures, duplicate dentures, inexpensive basic or affordable dentures and denture repairs. The cold cure acrylic resin is generally processed in an electrically heated pressure vessel. When fabricating a dental prosthesis with cold cure acrylic the waxed prosthetic teeth and cast are placed in a duplicating flask designed for a duplicating material made of either a two part free flowing silicone or melted reversible hydrocolloid to be poured into the duplicating flask creating a negative impression of the waxed prosthesis. When the duplicating material becomes rigid the cast and waxed teeth are separated from the duplicating material where in the wax is removed from the cast and cleaned from the teeth. Once teeth and cast are thoroughly cleaned they are reinserted into the impression material and cold cure acrylic poured in through access holes of the flask. The flask is then placed into the electrically heated pressure vessel and cured at an appropriate pressure and temperature according to manufacturers recommendations. The duplicating materials associated with the cold pour technique however have constraints.

Reversible hydrocolloids require time constraints to chop and melt the material and bring the material to an ideal operating temperature. The ideal operating temperature being a temperature which allows the material to easily flow into a duplicating flask and reflect the detail of the waxed prosthesis without melting the wax and damaging the precise dimensions of the waxed prosthesis. There are also cost constraints with the availability of expensive equipment such as hydrocolloid conditioners designed to melt the hydrocolloid and keep the material at a constant operating temperature all the while mixing the material to keep it from congealing. Also necessary are cold running water baths, which cool the material for removing the waxed prosthesis from the duplicating material in a timely manner. Hydrocolloid is also highly susceptible to distortion when removing the waxed cast from the flexible material and it has poor dimensional stability causing a possible changed in the vertical dimension, affecting the accuracy of the final prosthesis' occlusion.

Free flowing Addition silicones mimic the accuracy of reversible hydrocolloid with a high dimensional stability. No reaction by products are formed as long as the correct proportions of one to one A-silicone are used. To achieve accuracy it is recommended to have a homogeneous mixing of the material to avoid streaks and voids. There are manufacturer-mixing machines available but add to the expense already associated with the higher price material costs of free flowing A-silicone and its single use nature. Free flowing Addition silicones are also limited to a fairly low Shore hardness, usually in the low twenties and teens. Lab silicones with a lower Shore hardness will demonstrate lower stiffness; unfortunately decreased stiffness may allow the matrix to be easily deformed effecting vertical dimension.

SUMMARY OF THE INVENTION

The present invention comprises an improved dental flask and method that allows for traditional, inexpensive materials such as dental stone and lab putty to create a rigid and stable matrix surrounding a waxed form, allowing for the creation of a final prosthesis. By utilizing the dental reline jig with the improved dental flask it is possible to preserve the vertical dimension of the waxed formed prosthesis, recreating the accuracy of the established occlusion quickly and dependably without the cost of expensive equipment and materials. The improved dental flask allows for the reduction of production time and material costs in the processing of cold cure acrylic. The improved dental flask is repeatable and dependable technology that uses standard flask materials and processing techniques such as a durable stone matrix and the ability to boil out the wax form from the chamber due to the material's rigidity and insulating nature to the stone matrix.

DETAILED DESCRIPTION OF THE INVENTION

In accordance with the present method and invention, an improved dental flask is provided which enables an acrylic dental prosthesis to be processed within a dental reline jig using acrylic resin in the cold pour technique.

Figure 1:
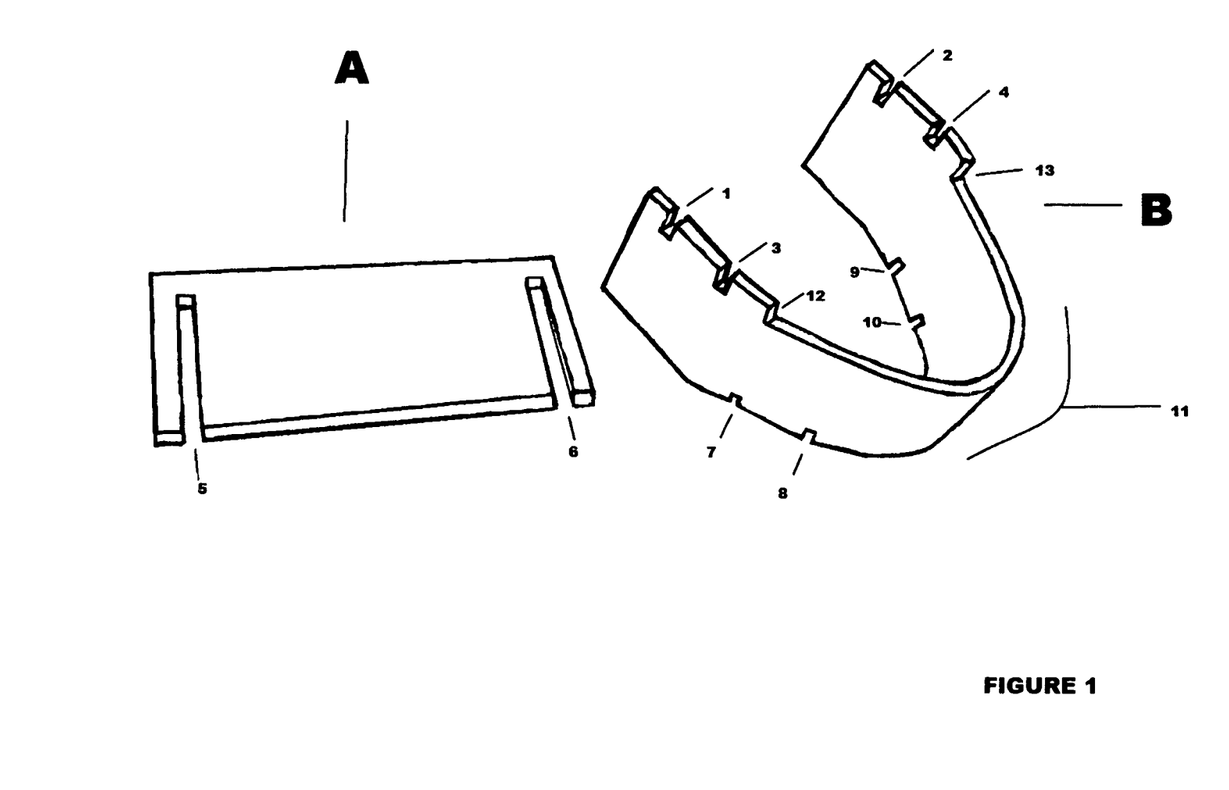
FIG. 1 is a perspective view of the improved dental flask and back plate.
Figure 2:
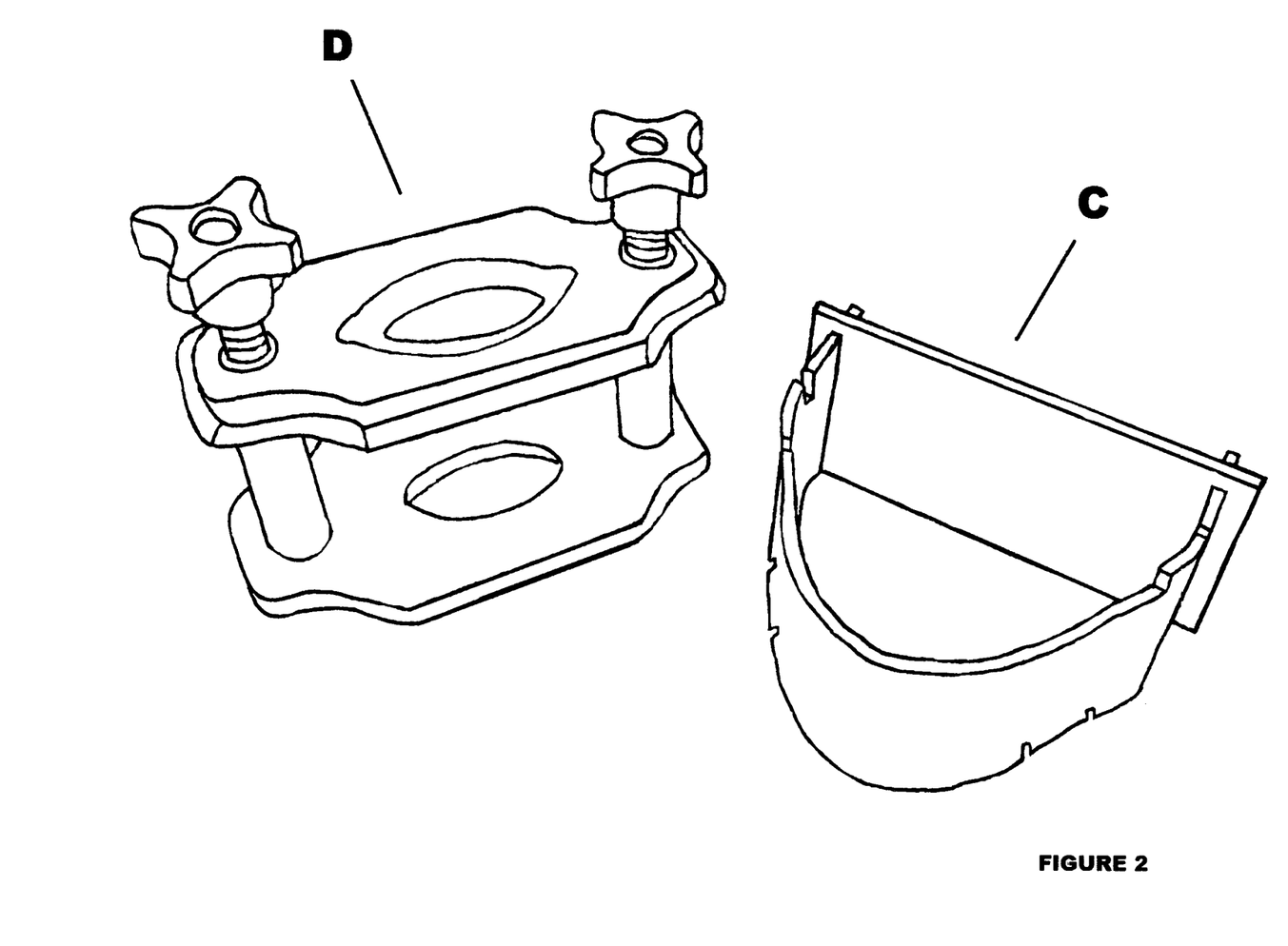
FIG. 2 is a perspective view of a dental reline jig and an assembled improved dental flask and back plate.
Figure 3:
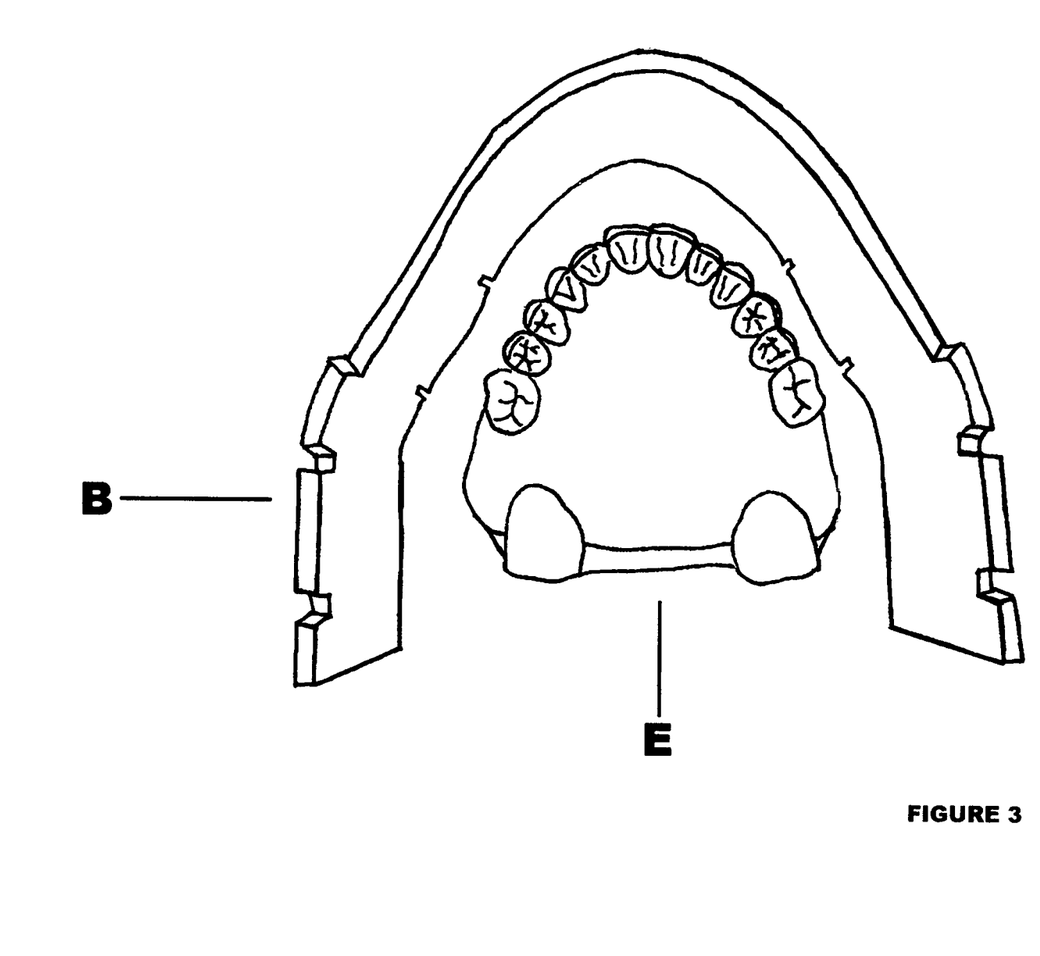
FIG. 3 is a top view of a waxed dental prosthesis with acrylic teeth placed within an improved dental flask.

An improved dental flask (B) is shown generally in FIG. 1 having four slots 1, 2, 3, and 4 formed into the top of the flask to allow for the assembly of the back plate (A) with engaging slots 5 and 6. The assembled improved dental flask and back plate (C) in FIG. 2 create an enclosed environment to hold the materials necessary for which to flask a waxed dental prosthesis (E) in FIG. 3. Installing the improved dental flask and back plate (C) into a dental reline jig (D) in FIG. 2 allows for the preservation of the vertical dimension relationship established with the articulation and wax try in of the waxed dental prosthesis (E) during processing.

Figure 4:
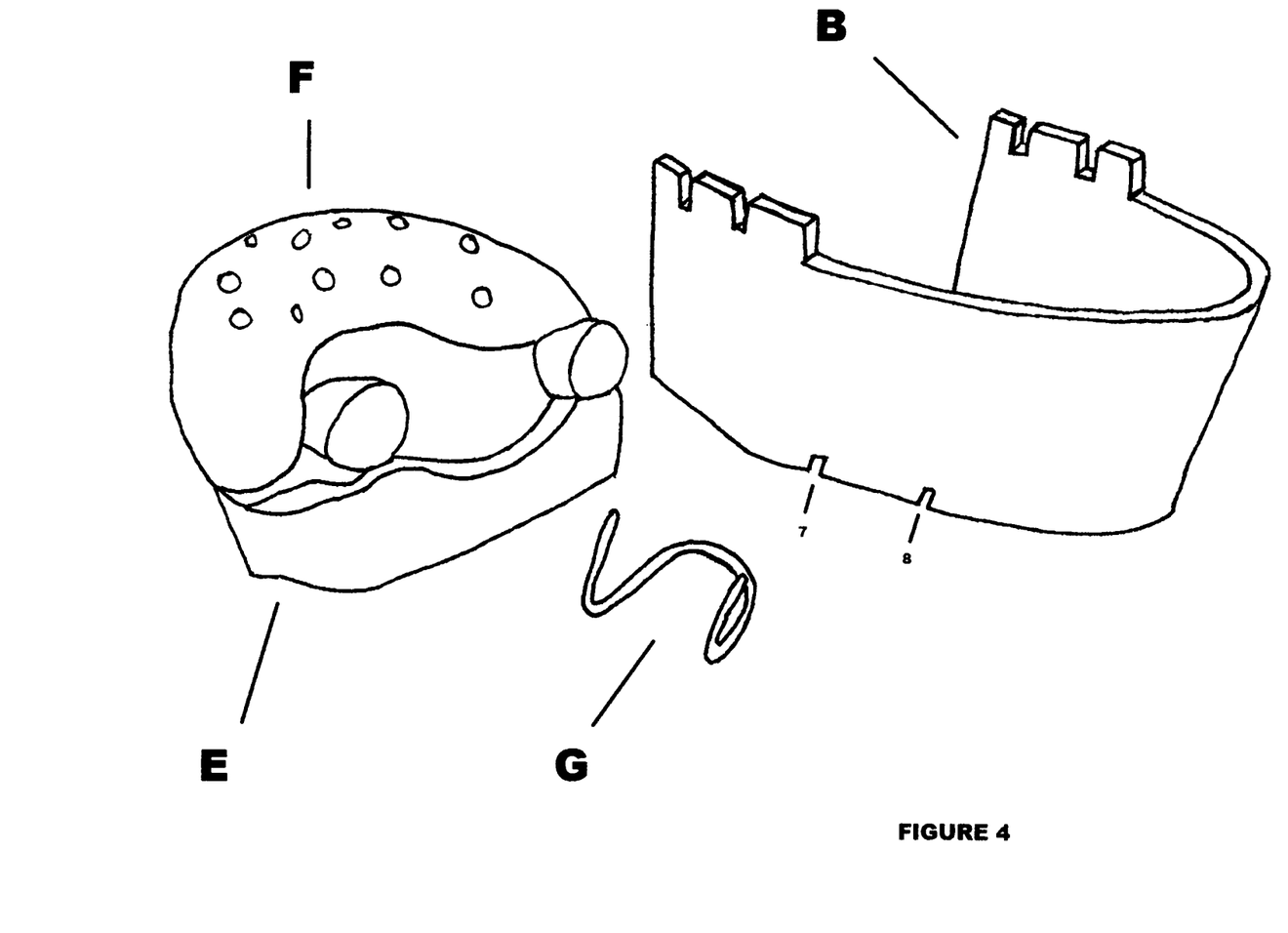
FIG. 4 is a perspective view of a waxed dental prosthesis with putty index over dentition, a wire bent for retention within the flask chamber and an improved dental flask.
Figure 5:
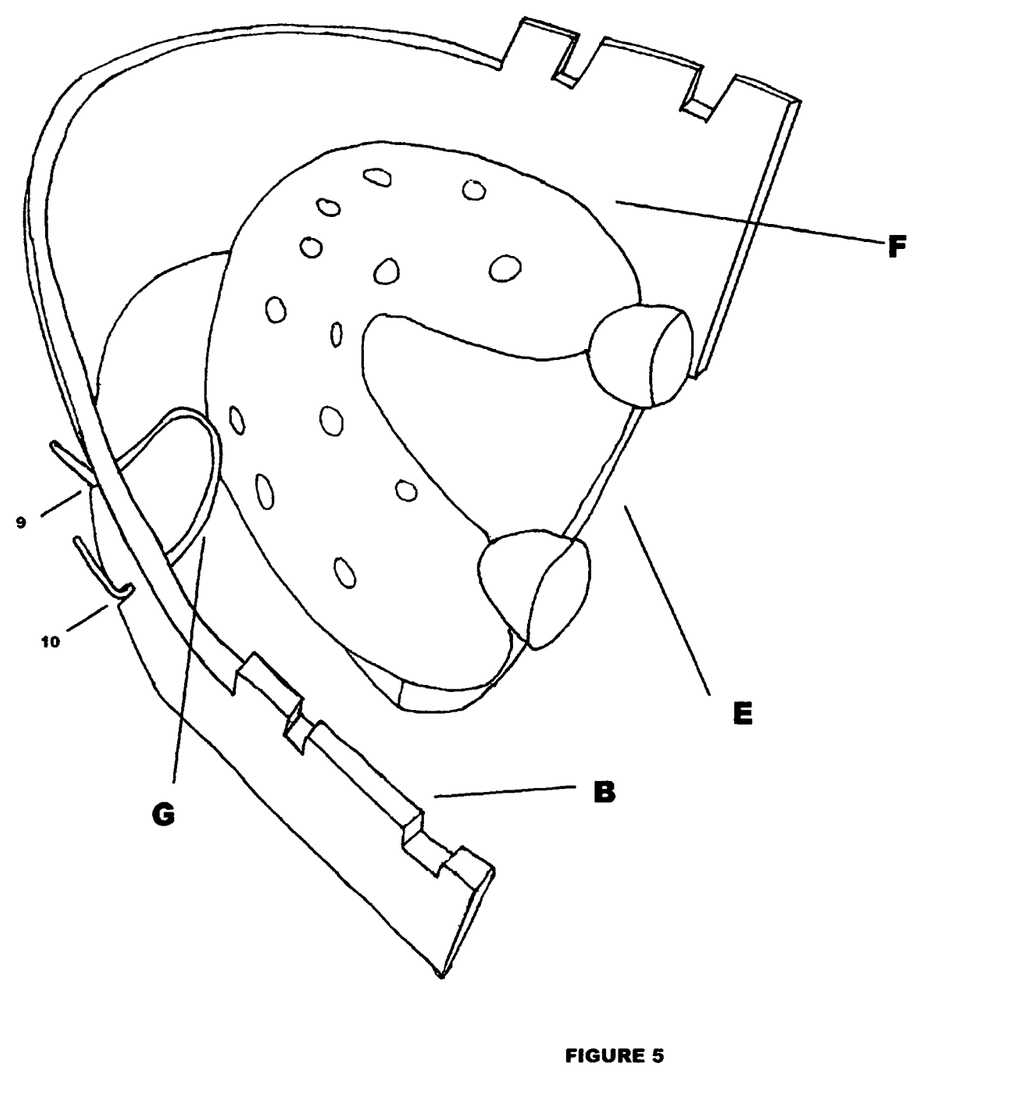
FIG. 5 is a top view of an improved dental flask and a waxed dental prosthesis with putty index within the flask chamber and incorporating the bent wire retention.

A putty matrix (F) FIG. 4 is indexed around the acrylic teeth of the waxed dental prosthesis (E) in a technique used to protect and preserve the detail and integrity of the wax up. The putty matrix (F) assists in the removal of acrylic teeth for cleaning and creating diatoric holes necessary in the cold pour technique. To retain the stone matrix used during the processing of an acrylic dental prosthesis within the improved dental flask and back plate (C) enclosure, a wire (G) in FIG. 4 is bent so as to engage the stone matrix and the improved dental flask (B). The wire (G) is placed through slots 9 and 10 in FIG. 5 on one side of the improved dental flask (B) and another wire similar to wire (G) is placed on the other side of the improved dental flask (B) through slots 7 and 8 in FIG. 4. The two wires (G) ensure that after the setting of the investment matrix the improved dental flask (B) remains attached throughout the boil out and processing stages when the back plate (A) is removed.

Figure 10:
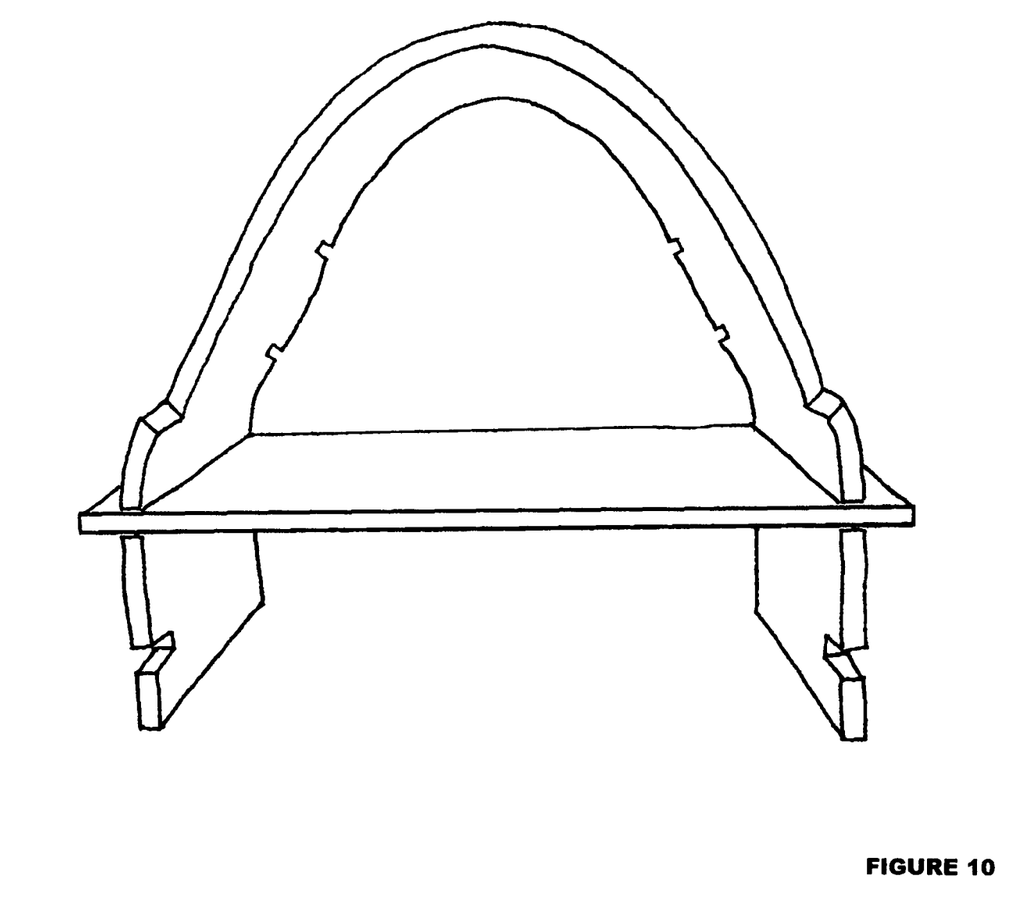
FIG. 10 is a top view of an assembled improved dental flask and back plate for small flask chamber.
Figure 11:
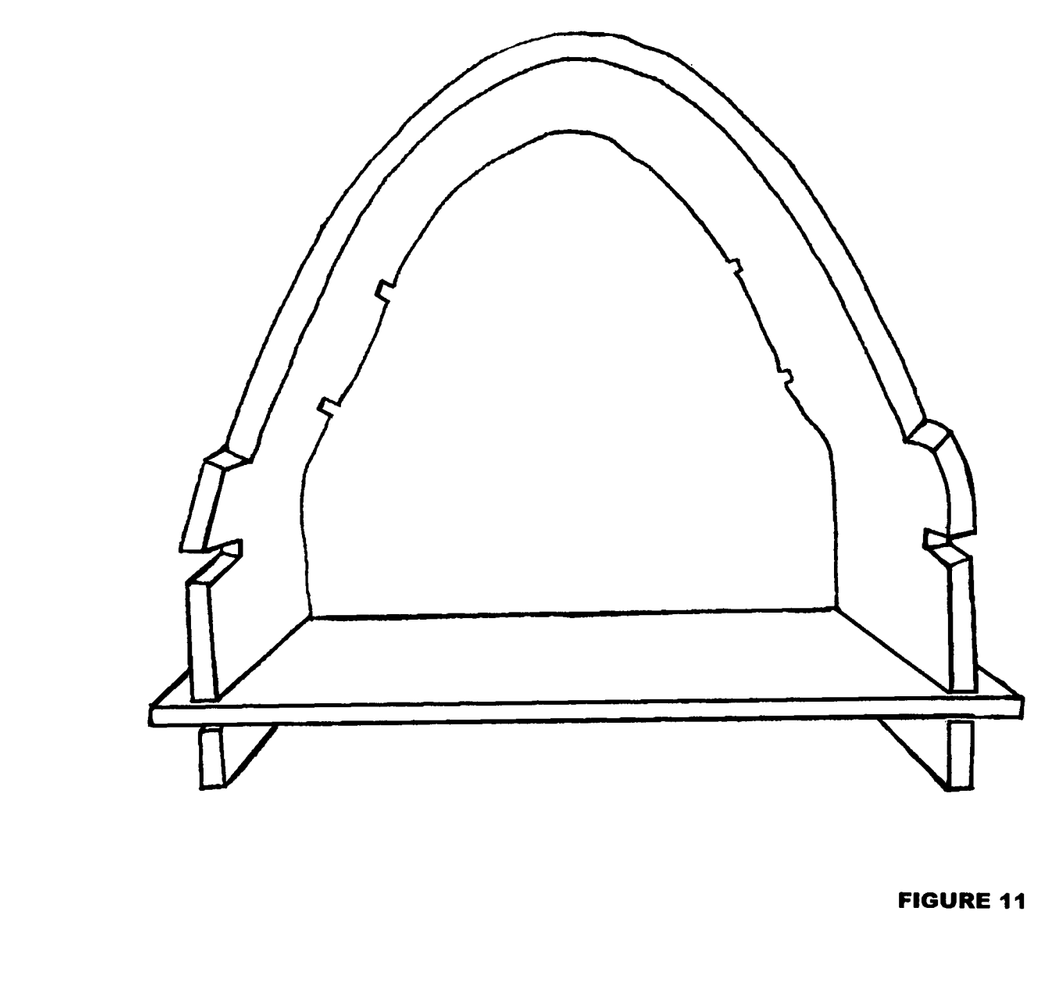
FIG. 11 is a top view of an assembled improved dental flask and back plate for large flask chamber.

The size of the waxed dental prosthesis' (E) cast model will determine the size needed of the improved dental flask and back plate (C). Inserting the back plate's (A) slots 5 and 6 into either slots 1 and 2 (large flask chamber FIG. 11) or slots 3 and 4 (small flask chamber FIG. 10) of the improved dental flask (B) allows for an appropriate amount of investment material to flow around the waxed dental prosthesis (E) for desired strength and rigidity of the matrix.

Once assembled the improved dental flask and back plate (C) are placed on a smooth flat surface. The waxed dental prosthesis' (E) cast must be trimmed to slightly less then 90 degrees, beaded with utility rope wax and brushed with model separator (tinfoil substitute) to ease in it's removal from the flask after the boil out stage. The back of the waxed dental prosthesis (E) and putty matrix (F) is centered into the flask chamber against the back plate (A) in FIG. 6. This allows for uniformity of investment material in the flask chamber and access to the sprue holes and cast of the waxed dental prosthesis (E) when the back plate (A) is removed.

Figure 6:
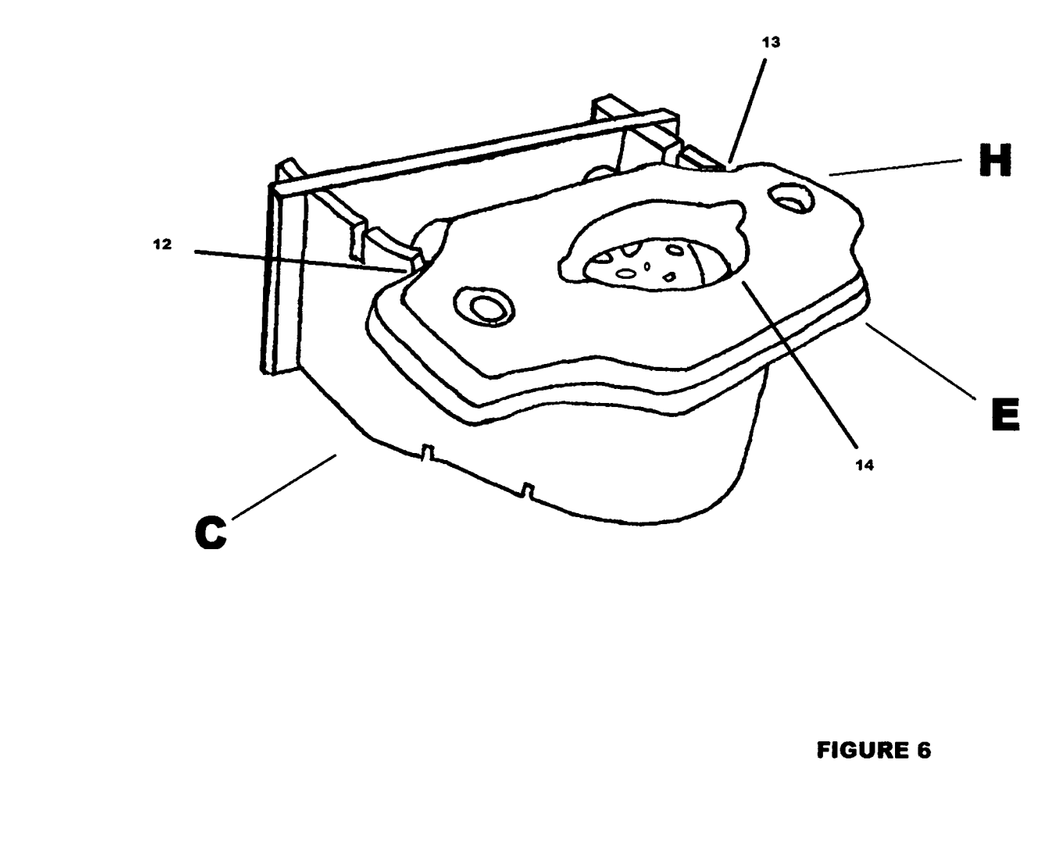
FIG. 6 is a perspective view of a waxed dental prosthesis with putty index within the flask chamber and a top half of a dental reline jig installed on an assembled improved dental flask and back plate.

The investment material is poured into the flask chamber encompassing the retention wires (G), the waxed dental prosthesis (E), and putty matrix (F) up to the level of the improved dental flask's (B) relief area 11 FIG. 1. The top half of the dental reline jig (H) in FIG. 6 is placed in relief area 11 on top of improved dental flask and back plate (C) evenly centered against plate stops 12 and 13 in FIG. 6. And a remainder of the investment mix is placed into the flask chamber through the top half of the dental reline jig's (H) retention hole 14 in FIG. 6.

Figure 7:
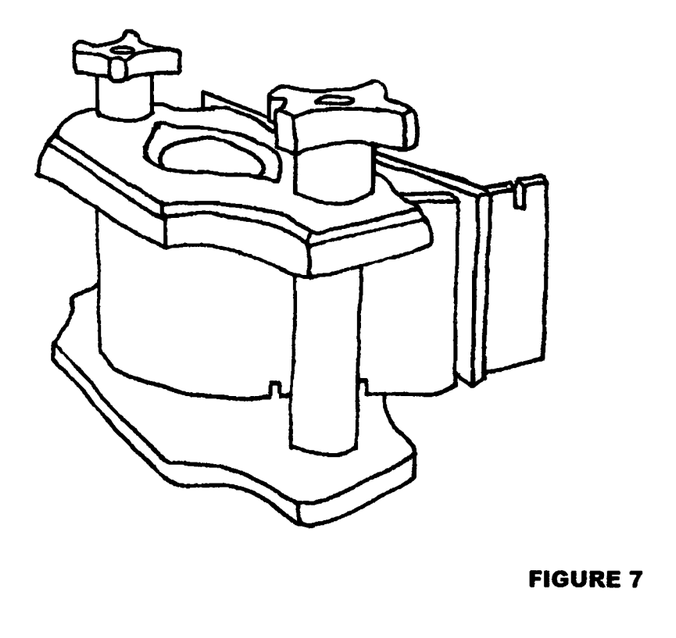
FIG. 7 is a side view of an assembled improved dental flask and back plate installed within a dental reline jig.
Figure 8:
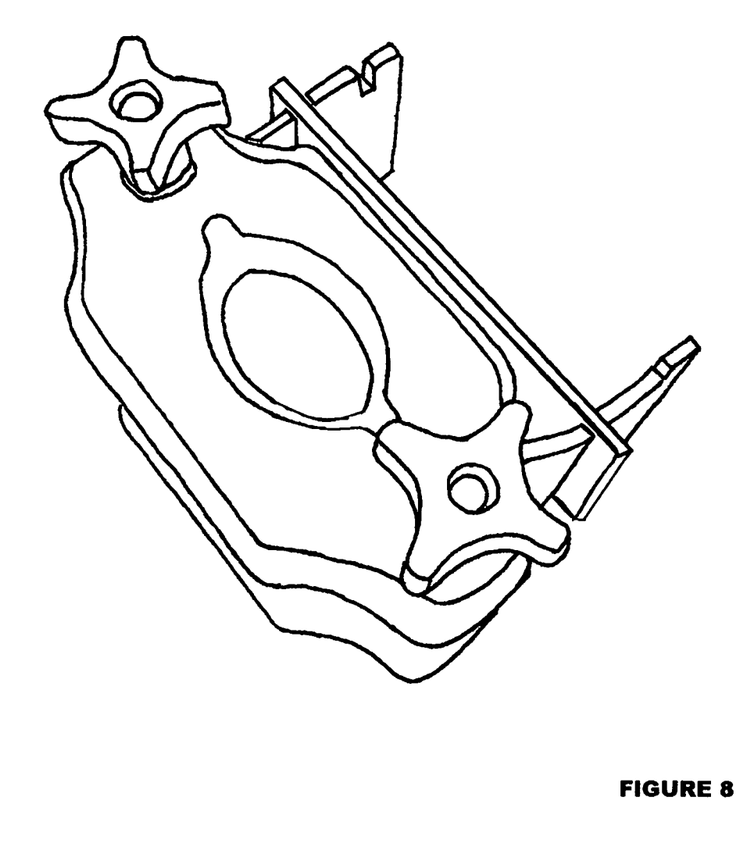
FIG. 8 is a top view of an assembled improved dental flask and back plate installed within a dental reline jig.
Figure 9:
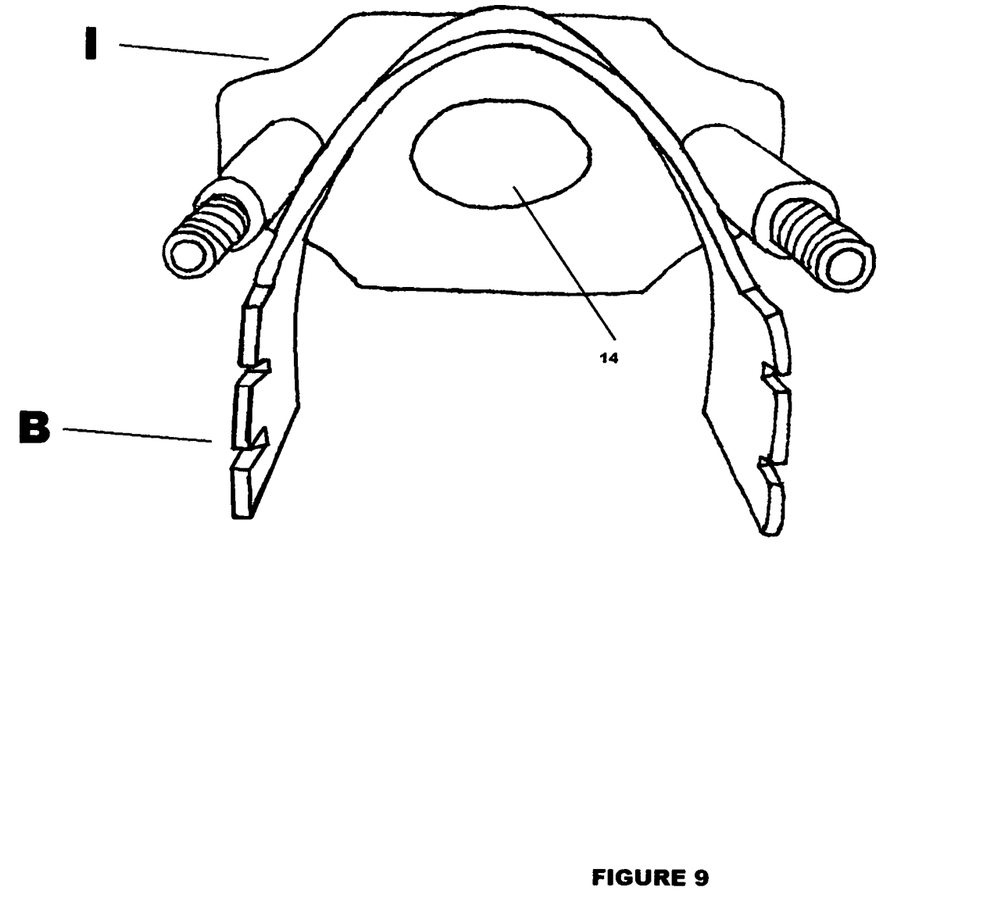
FIG. 9 is a top view of an improved dental flask installed within the bottom half of a dental reline jig.

Once the investment is cured according to manufacturers instructions the back plate (A) is removed and the excess stone cleaned from around the sprue holes and the back area of the waxed dental prosthesis' (E) cast. The waxed dental prosthesis' (E) cast if not already indexed at this time should be and all other areas of the flask's investment base needs to be brushed with model separator (tinfoil substitute). The two halves of the dental reline jig (D) are then reassembled with dental mounting stone attaching the bottom half of the dental reline jig (I) FIG. 9 through retention hole 14 to flask's base. FIG. 7 and FIG. 8.

What is claimed is:

1. A dental flask, comprising:
   an arch shaped plate configured to fit within confines of a dental reline jig;
   a removable back plate;
   wherein the arch shaped plate is recessed in a center region on a top side of the arch shaped plate so as to provide a stop and landing area for a top of the dental reline jig;
   wherein the back plate has two notches on opposite sides of the back plate configured to slide over two first notches on a top side of a back region of the arch shaped plate to create an enclosed chamber; and
   wherein the arch shaped plate has four lower notches on a bottom side of the arch shaped plate for inserting wires for retaining the matrix material to the dental flask.

2. The dental flask and back plate of claim 1, where in the flask and the back plate are manufactured from aluminum in order to contain a matrix material and transfer heat from the matrix material.

3. The dental flask of claim 2, wherein the aluminum of the arch shaped plate is cut and formed into an arch shape to fit between posts of a dental reline jig.

4. The dental flask of claim 2, wherein the back plate is cut to a length that when assembled create an enclosed flask chamber.

5. The dental flask of claim 1, wherein the dental flask further comprises two second notches on opposite sides of the top side of the back region of the arch shaped plate, allowing for two enclosed chamber sizes of the dental flask.

6. The dental flask of claim 1, wherein the lower notches are located in an area of the bottom side of the arch shaped plate so as not to interfere with posts of the dental reline jig and small enough so as not to leak out matrix material.

* * * * *